United States Patent
Geisendoerfer et al.

(10) Patent No.: US 7,268,251 B2
(45) Date of Patent: Sep. 11, 2007

(54) METHOD FOR PRODUCING (METH) ACRYLIC ACID ESTERS

(75) Inventors: Matthias Geisendoerfer, Neustadt (DE); Albrecht Dams, Wachenheim (DE); Gerhard Nestler, Vienna (AT)

(73) Assignee: BASF Aktiengesellschaft, Ludwigshafen (DE)

( * ) Notice: Subject to any disclaimer, the term of this patent is extended or adjusted under 35 U.S.C. 154(b) by 601 days.

(21) Appl. No.: 10/479,562

(22) PCT Filed: May 28, 2002

(86) PCT No.: PCT/EP02/05820

§ 371 (c)(1),
(2), (4) Date: Dec. 4, 2003

(87) PCT Pub. No.: WO02/100814

PCT Pub. Date: Dec. 19, 2002

(65) Prior Publication Data

US 2004/0171868 A1    Sep. 2, 2004

(30) Foreign Application Priority Data

Jun. 8, 2001 (DE) ................ 101 27 939

(51) Int. Cl.
  *C07C 69/52* (2006.01)
(52) U.S. Cl. ................................... 560/205
(58) Field of Classification Search ........... 560/205
  See application file for complete search history.

(56) References Cited

U.S. PATENT DOCUMENTS

| 3,686,268 A | 8/1972 | Jobert et al. |
| 3,872,161 A | 3/1975 | Fukuchi et al. |
| 6,818,791 B2 * | 11/2004 | Martin et al. ........... 560/205 |

FOREIGN PATENT DOCUMENTS

| BR | 8 701 337 | 9/1988 |
| DE | 1 067 806 | 10/1959 |
| DE | 1 142 868 | 1/1963 |
| DE | 1 956 308 | 7/1970 |
| DE | 2 008 618 | 9/1970 |
| DE | 2 317 226 | 10/1974 |
| DE | 28 05 702 | 8/1978 |
| DE | 100 26 644 | 12/2001 |
| EP | 0 118 639 | 9/1984 |
| EP | 0 143 639 | 6/1985 |
| EP | 0 160 427 | 11/1985 |
| EP | 0 298 867 | 1/1989 |
| EP | 0 210 907 | 9/1989 |
| EP | 0 736 510 | 10/1996 |
| EP | 0 902 017 | 3/1999 |
| EP | 0 906 902 | 4/1999 |
| EP | 0 960 877 | 12/1999 |
| JP | 7-53449 | 2/1995 |

OTHER PUBLICATIONS

ORGANIKUM, vol. 17, Veb DT. Verlag Der Wissenschaften, Berlin, pp. 506-507 1988.
Ullmann's Encyclopedia of Industrial Chem., 6th ed. Electronic Release, "Acrylic Acid and Derivatives" 1999.

* cited by examiner

*Primary Examiner*—Rebecca Anderson
*Assistant Examiner*—Rei-tsang Shiao
(74) *Attorney, Agent, or Firm*—Oblon, Spivak, McClelland, Maier & Neustadt, P.C.

(57) ABSTRACT

The invention relates to a method for producing (meth) acrylic acid esters IV by means of transesterification of a (meth)acrylic acid ester I with an alcohol $R^2OH$ comprising at least one more carbon atom than the alcohol constituents ($R^1O$—) in the (meth)acrylic acid ester I to be subjected to transesterification, in the presence of a catalyst or a catalyst mixture. Either essentially the (meth)acrylic acid ester I is separated and then the catalyst used is separated by distillation (catalyst separation), or the catalyst used is separated by distillation first (catalyst separation), and then essentially the (meth)acrylic acid ester I is separated, from the reaction product of the transesterification. Constituents from the mixture obtained, which have a lower boiling point than the (meth)acrylic acid ester IV, are essentially separated by distillation (separation of constituents at low boiling point), and the (meth)acrylic acid ester IV is then purified by distillation (purification by distillation).

37 Claims, 1 Drawing Sheet

Fig. 1

METHOD FOR PRODUCING (METH) ACRYLIC ACID ESTERS

The present invention relates to a process for the continuous preparation of higher (meth)acrylates by reacting a lower (meth)acrylate with a higher alcohol.

The preparation of (meth)acrylates by transesterification in the presence of acidic or basic catalysts is generally known. Catalysts proposed in particular are titanium alcoholates whose alkyl groups are $C_1$-$C_4$-alkyl radicals, e.g. tetramethyl, tetraethyl, tetraisopropyl, tetrapropyl, tetraisobutyl and tetrabutyl titanate (cf. for example EP-B1 298 867, EP-A2 960 877). Inter alia, titanium phenolates (German Laid-Open Application DOS 2,008,618), metal chelate compounds of, for example, hafnium, titanium, zirconium or calcium, alkali metal and magnesium alcoholates, organic tin compounds or calcium and lithium compounds, for example oxides, hydroxides, carbonates or halides thereof, have furthermore been proposed as catalysts.

Since the transesterification is known to be an equilibrium reaction, one of the starting materials must be used in a large excess and/or one of the reaction products must be removed from the equilibrium in order to achieve economical conversions. As a rule, the lower alkanol liberated during the transesterification (alcohol component having the lower boiling point) is therefore separated off by distillation. The disadvantage here is that the alkanols liberated, usually methanol or ethanol, form an azeotropic mixture with the corresponding (meth)acrylates (methyl or ethyl (meth)acrylate) and thus cannot be separated directly by distillation.

For ecological and economic reasons, the reuse of the azeotropic mixture or its individual components (alkanol and (meth)acrylate) is however advantageous.

The direct use of the azeotropic mixture or the recovery and recycling of the starting ester may be complicated or even prevented by the entrainment of impurities, for example by the catalyst.

By using titanium tetraisopropylate or butylate, the most usual transesterification catalysts, for example, isopropanol and butanol are entrained as impurities (German Laid-Open Application DOS 2,008,618, page 2).

If titanium, zirconium or hafnium acetylacetonate are used as catalysts, for example, acetylacetone is present in the reaction mixture.

Owing to the small boiling point difference or formation of azeotropic mixtures, some of the impurities are difficult to remove and lead in some cases to the formation of further byproducts (transesterification reactions, addition at the double bond of the esters).

German Laid-Open Application DOS 2,008,618 therefore recommends using titanium phenolates as catalysts. However, these have to be prepared by a very inconvenient and expensive procedure and, being solids, are moreover difficult to handle.

In principle, such impurities could also be avoided by using titanates of the lower alkanols $R^1OH$ (cf. equation I) whose alkyl (meth)acrylates are used (e.g. titanium tetramethylate where methyl (meth)acrylate is used). EP-B1 298 867 describes, for example, the transesterification of ethyl acrylate with dimethylaminoethanol in the presence of titanium tetraethanolate. These titanates are expensive and extremely sensitive to hydrolysis (German Laid-Open Application DOS 2,008,618, page 2) and are therefore of no industrial importance.

It is furthermore known that the mixture or azeotropic mixture obtained in the preparation of basic (meth)acrylates by transesterification and comprising starting ester and the alkanol component of the starting ester is contaminated by basic compounds (e.g. amines) (EP-A2 906 902). Accordingly, the mixture can be utilized without problems in the preparation of the starting ester only when it is purified beforehand. EP-A2 906 902 proposes an expensive treatment with acidic ion exchange resins.

The disadvantage here is in particular the fact that the ion exchanger must be regenerated in an environment-polluting manner (production of wastewater) and/or disposed of.

Since the formation of azeotropic mixtures or mixtures of starting ester and starting alkanol accordingly constitutes a major disadvantage, various methods for avoiding and/or working up these azeotropic mixtures or mixtures of alkanol and (meth)acrylate have been proposed.

In the literature, for example in EP-B1 210 907, the use of assistants, such as benzene, hexane, cyclohexane, etc., which form hetero azeotropic mixtures with the lower alkanols liberated is proposed. The lower alkanol liberated during the transesterification is separated off by distillation with the assistant as an azeotropic mixture, the condensate separating into two phases. The phase which contains the assistant is recycled to the transesterification and the alkanol phase saturated with assistant is discharged. Since an assistant is required and the discharged alkanol phase has to be purified before being reused, however, these processes are of no economic importance.

In addition, various processes for separating/working up these alkanol/ester azeotropic mixtures or mixtures have been proposed.

EP-A1 736 510 proposes carrying out the separation of the mixture of methanol and methyl (meth)acrylate and possibly water with the aid of aliphatic hydrocarbons which form an azeotropic mixture with methanol. However, the use of an additional assistant makes this process too uneconomical.

DE-A1 23 17 226 proposes separating the azeotropic mixture formed from alkanol and the corresponding (meth)acrylate by washing out the alkanol by treatment with water. The process is not economical since the resulting aqueous alkanol solution has to be disposed of or worked up, and the ester phase has to be dried before being recycled to the transesterification.

EP-A2 143 639 recommends the separation of these azeotropic mixtures with complex-forming salts, e.g. LiCl, and an extracting agent. The process is uneconomical since it produces wastewaters and requires a plurality of distillation steps.

In principle, azeotrope formation can also be prevented by carrying out the transesterification of the lower ester with at least stoichiometric amounts of a metal alcoholate of the higher alkanol. The resulting metal alcoholate of the lower alkanol is isolated and is converted by reaction with the higher alkanol back into the corresponding metal alcoholate, which is recycled to the transesterification (EP-A1 118 639, EP-A2 160 427). However, the process requires large amounts of metal alcoholate and is therefore of no industrial importance.

A further problem is the formation of Michael adducts in the transesterification and working-up of the transesterification reaction mixture. Here, Michael adducts are understood as meaning the compounds formed by addition of alcohols at the double bond of the (meth)acrylates (EP-A2 906 902, pages 8 and 9).

It is generally known that this addition (cf. equation II) takes place in particular in the presence of alkaline catalysts (Organikum, 17th edition, page 506, VEB Deutscher Verlag der Wissenschaften, Berlin 1988).

(Equation II)

In the transesterification according to equation 1, substantially the adducts (II) and (III) play a role The results of this adduct formation are a lower yield and a greater distillation effort for obtaining the desired ester in high purity.

As is generally known, the formation of the adducts according to the general equation II can be reduced by keeping the concentration of free alkanol as low as possible. EP-A2 906 902 therefore proposes adding the main amount of the alkanol continuously during the transesterification and not allowing the concentration of the alkanol to increase above 25 mol %.

Furthermore, the same publication proposes keeping the temperature during the removal of low boilers and catalyst by distillation in the range of from 60 to 120° C. in order to reduce the additional formation of Michael adducts.

A further problem is the instability of some titanium alcoholates at relatively high temperatures. The result is fouling of the apparatus walls.

This is particularly disadvantageous because, owing to their relatively low activity, elevated temperatures are required in transesterification in order to obtain economical conversions or reaction times (EP-A2 160 427, page 2, lines 23 to 30). This in turn can lead to increased polymer formation and fouling.

It is also known that (meth)acrylic acid compounds have a considerable tendency to polymerization, very particularly if heat acts on them (cf. for example Ullmann's Encyclopedia of Industrial Chemistry, 6th ed, 1999 Electronic Release, Section: Acrylic Acid and Derivatives). Especially in the preparation and the distillative purifications, they are exposed to temperatures which can easily initiate an undesired polymerization.

Another problem is the loss of activity which the titanium alcoholates suffer in the course of time (DE-A 28 05 702, page 5, lines 12 to 21). In order to obtain economical conversions, the amount of catalyst and/or the reaction time must be increased. In view of the instability of the titanates and the byproduct formation and polymer formation, this is known to be disadvantageous.

It is also generally known that alkyl titanates catalyze the polymerization of (meth)acrylates and may therefore give rise to the formation of polymer during the alcoholysis or transesterification and the working-up of the transesterification mixture (German Laid-Open Application DOS 2,008, 618, page 3) or may influence the action of stabilizers (German Patent 1,067,806, column 1, lines 25 to 40).

Soiling of the apparatuses, blockage of pipes and pumps and fouling of column trays or internals and heat exchanger surfaces are as a rule the result of polymer formation. Cleaning of the plants is a complicated procedure which is expensive owing to, for example, the downtimes and is environmentally polluting, for example because of the resulting wastewaters from cleaning. The yield and the availability of the plants (time-on-stream) are thus also reduced to a great extent.

German Patent 1,067,806 therefore proposes carrying out the transesterification under pressure and at 180-250° C. in order as far as possible to achieve short residence times. On the other hand, the use of stabilizers or stabilizer mixtures is proposed, for example aminophenols, hydroquinone, hydroquinone monomethyl ether, phenothiazine, etc., with or without the addition of oxygen or air (Japanese Preliminary Published Application 53449/95). However, working under pressure requires expensive apparatus and safety technology and is therefore uneconomical.

German Laid-Open Application DOS 1,965,308 proposes a mixture of phenothiazine and diethylhydroxylamine for stabilization, but an uneconomically large amount of 1-3%, based on alkanol, is required. However, complete avoidance of polymer formation is also not possible thereby.

Since, as described above, the conventional transesterification catalysts adversely affect the stability of the reaction mixture, the removal of the catalyst before the working-up by distillation is expressly recommended, for example by washing with water (German Laid-Open Application DOS 2,805,702).

However, the removal of the catalyst, for example of titanium alcoholates, is very expensive since it requires filtration after the hydrolytic cleavage of the catalyst.

DE-A 1 142 868 therefore recommends the use of the polymeric titanates which are insoluble in the reaction mixture and can also be used as solid. Owing to their expensive preparation, these catalysts have not become important commercially.

A further problem occurs in the preparation of dialkylaminoethyl (meth)acrylates by transesterification of dialkylaminoethanols:

The preparation of dialkylaminoethanols is known to be carried out by reacting ethylene oxide in the liquid phase at from 100 to 150° C. with the corresponding dialkylamines. Byproducts which occur here are in general higher homologs, which can be substantially separated off by distillation, and byproducts, e.g. vinyloxyethanol and ethylene glycol, which can be separated off by distillation only with very great difficulty and are therefore present in traces in the dialkylaminoethanols.

Transesterification of these components leads to ethylene glycol di(meth)acrylate and vinyloxyethyl (meth)acrylate, which may occur as secondary components in the preparation of alkylaminoethyl (meth)acrylates and contain two unsaturated groups. These secondary components therefore act as crosslinking agents in the polymerization. This is extremely disadvantageous since the polymerization and the quality of the polymers are adversely affected as a result, for example by gel formation. Moreover, they influence the shelf life.

Owing to the stability and polymerization problems described, the working-up of the transesterification mixture or the isolation of the desired ester is as a rule carried out in a plurality of distillation stages.

EP-A2 906 902 describes, for example, a process for the preparation and isolation of alkylaminoalkyl (meth)acrylates, which substantially comprises the following stages:
1. Batchwise transesterification in the presence of the catalyst dibutyltin dioxide and of the stabilizer phenothiazine, the main amount of the alkylaminoalkanol being added after the start of the reaction in a manner such that its concentration in the reaction mixture does not exceed 25 mol %.
2. Distillative removal of the lower alkanol, formed during the transesterification, as an azeotropic mixture with the lower (meth)acrylate via a column, the distillate being subjected, if required, to a further distillation.
3. Treatment of the distillate, which mainly comprises lower alkanol and lower (meth)acrylate, with an acidic cation exchanger. The basic impurities (amines) which prevent use of the distillate in the preparation of the lower ester by poisoning the catalyst used therein are separated off thereby.
4. Distillative separation of the reaction mixture into a top product, mainly comprising desired ester, lower alkanol and starting materials, and a bottom product, which substantially comprises catalyst, stabilizer, Michael adducts and polymers and may be reused in the transesterification. If the catalyst loses its activity, it is disposed of.
   Alternatively, the catalyst removal may be effected in two stages, first the lower (meth)acrylate being separated off via the top of a column and recycled to the transesterification. In a second distillation column, the desired ester and remaining low boilers are separated off as top product and the catalyst-containing bottom product is, if desired, reused in the transesterification.
5. The distillate containing the desired ester is separated in a further distillation stage into a top product (aminoalkanol, lower ester), which can be reused in the transesterification, and a bottom product which contains the desired ester.
6. Finally, in a further distillation step (distillative purification), the desired ester is isolated in a purity of 99.8% from the bottom product containing said ester.
7. From the bottom product of the distillative purification, which still contains desired ester, a part of the desired ester is isolated in a distillation, preferably a thin-film distillation, and is fed to the low boiler distillation. The bottom product is disposed of.
   Among the disadvantages of the process are
   that the transesterification is effected batchwise,
   that the dialkylaminoalkanol has to be added to the reactor over a long period (4 hours),
   that long reaction times (7-8 hours) are required, which promotes the formation of byproducts and of polymer,
   that the azeotropic mixture has to be purified in a technically complicated manner over an ion exchanger bed, which is environmentally polluting owing to the necessity of washing and regeneration,
   that the yield is low (about 33%, based on dimethylaminoethanol used, cf. example III-1) and
   that the residues are not worked up to recover useful products.

EP-A2 960 877 describes a continuous process for the preparation of dialkylaminoalkyl (meth)acrylates by transesterification of methyl or ethyl (meth)acrylate with dialkylaminoalkanols in the presence of tetraethyl, tetrabutyl or tetra(2-ethylhexyl) titanate. The transesterification is effected there in a stirred reactor and the working-up of the reaction mixture is effected in the following steps:
1. The reaction mixture is separated in a distillation unit into a top product, which substantially comprises the desired ester and the low boilers, and a bottom product which mainly comprises high boilers, catalyst and a little desired ester.
2. The bottom product can, if required, be purified in a thin-film evaporator, the distillate being recycled to the transesterification. The catalyst-containing bottom discharge is eliminated from the process.
3. The top product containing the desired ester is separated in a further distillation step into a low boiler fraction, which is recycled to the reactor, and a bottom product, predominantly desired ester.
4. In a further distillative purification step, the desired ester is isolated (purity 99.8%) as top product from the bottom product. The resulting residue is recycled to the low boiler removal.

This process has, inter alia, the following disadvantages:
The transesterification is effected in a stirred reactor which, owing to its moving parts, requires repairs
The alkanol component of the catalyst leads to impurities (cf. EP-A2 960 877, page 2, lines 49 to 50)
No utilization of the distillate separated off at the reactor and hence a loss of useful products
No utilization of the resulting high boilers (e.g. Michael adducts or catalyst).

It is an object of the present invention to provide a process which is free of said weaknesses and fulfills the following criteria:
1. The starting materials (catalyst, stabilizer, lower (meth)acrylate) should be economical, easy to handle and available in industrial quantity.
2. The catalyst should be stable at elevated temperatures and in the presence of small amounts of water.
3. The loss of activity of the catalyst should be small and said catalyst should be capable of being reused without problems.
4. No alcohol foreign to the system should be introduced into the transesterification via the transesterification catalyst.
5. Long times-on-stream of the plant, i.e. very few polymerization problems and use of apparatuses which require very little repair.
6. Direct reuse or utilization of the resulting mixture or azeotropic mixture of lower alkanol and the corresponding ester.
7. Substantial recovery of the remaining useful products from the waste streams and from the byproducts.
8. The transesterification should preferably be operated continuously.
9. The desired ester should have a high purity (at least 99.9%) and, in the case of the preparation of the dialkylaminoethyl (meth)acrylates, the formation of ethylene glycol di(meth)acrylate and vinyloxyethyl (meth)acrylate should be reduced, as far as possible, to below 100 ppm.
10. The amounts of waste should be very small and easy to handle.
11. Conversion and yield should be high (>95%).
12. The residence times should be short.
13. The overall process should be technically simple and economical.

We have found that this object is achieved by a process for the preparation of (meth)acrylate IV by transesterification of a (meth)acrylate I with an alcohol $R^2OH$ which has at least one carbon atom more than the alcohol component ($R^1O-$)

in the (meth)acrylate I to be transesterified, in the presence of a catalyst or catalyst mixture, wherein, from the discharge of the transesterification reaction, either first substantially (meth)acrylate I is separated off and is then separated by distillation from the catalyst used (catalyst removal), or is first separated by distillation from the catalyst used (catalyst removal) and then substantially (meth)acrylate I is separated off and then components having a lower boiling point than the (meth)acrylate IV are substantially separated from the resulting mixture by distillation (low boiler removal) and then the (meth)acrylate IV is purified by distillation (distillative purification).

We have also found that the stability of the dialkylaminoethyl (meth)acrylates prepared by basic transesterification of lower (meth)acrylates with dialkylaminoethanols depends decisively on the content of the byproducts in the dialkylaminoethanol used.

The novel process is carried out in general as follows:

$R^1$, $R^2$ and $R^3$ may each be aromatic, aliphatic or cycloaliphatic, straight-chain or branched, saturated or unsaturated and may contain hetero atoms or aromatic substituents.

Preferably,

R is H, $CH_3$, $R^1$ is $C_1$-$C_4$-alkyl, $R^2$ is $C_3$-$C_{12}$-alkyl or $C_2$-$C_{12}$-alkyl substituted by an $NR^3{}_2$ group and $R^3$ is $C_1$-$C_6$-alkyl, it being possible for N, together with the substituent $R^3$, also to form a five- to seven-membered ring and for the substituents $R^3$ to be identical or different.

$R^1$ should contain at least one carbon atom less than $R^2$; preferably, the boiling point of the alcohol $R^2OH$ under the chosen reaction conditions should be at least 20° C. above that of $R^1OH$.

$R^2$ is, for example, n-propyl, isopropyl, allyl, n-butyl, 1-methylpropyl, 2-methylpropyl, tert-butyl, n-pentyl, 1-methylbutyl, 2-methylbutyl, 3-methylbutyl, 2,2-dimethylpropyl, n-hexyl, 1-methylpentyl, 2-methylpentyl, 3-methylpentyl, 4-methylpentyl, 1,1-dimethylbutyl, 2,2-dimethylbutyl, 3,3-dimethylbutyl, 1,2-dimethylbutyl, n-heptyl, 1-methylhexyl, 2-methylhexyl, 3-methylhexyl, 4-methylhexyl, 1,2-dimethylpentyl, 1,3-dimethylpentyl, 1,1-dimethylpentyl, 1,1,2,2-tetramethylpropyl, benzyl, n-octyl, 2-ethylhexyl, n-nonyl, 1-methyloctyl, 2-methyloctyl, n-decyl, n-undecyl, 1-methyldecyl, 2-methyldecyl, n-dodecyl, 2,4-diethyloctyl, cyclopentyl, cyclohexyl, 4-tert-butylcyclohexyl, cycloheptyl, cyclododecyl, 2-(dimethylamino)ethyl, 3-(dimethylamino)propyl, 4-(dimethylamino)butyl, 5-(dimethylamino)pentyl, 6-(dimethylamino)hexyl, 8-(dimethylamino)octyl, 10-(dimethylamino)decyl, 12-(dimethylamino)dodecyl, 2-(diethylamino)ethyl, 3-(diethylamino)propyl, 4-(diethylamino)butyl, 5-(diethylamino)pentyl, 6-(diethylamino)hexyl, 8-(diethylamino)octyl, 10-(diethylamino)decyl, 12-(diethylamino)dodecyl, 2-(diisopropylamino)ethyl, 3-(diisopropylamino)propyl, 4-(diisopropylamino)butyl, 5-(diisopropylamino)pentyl, 6-(diisopropylamino)hexyl, 8-(diisopropylamino)octyl, 10-(diisopropylamino)decyl, 12-(diisopropylamino)dodecyl, 2-(dibutylamino)ethyl, 3-(dibutylamino)propyl, 4-(dibutylamino)butyl, 5-(dibutylamino)pentyl, 6-(dibutylamino)hexyl, 8-(dibutylamino)octyl, 10-(dibutylamino)decyl, 12-(dibutylamino)dodecyl, 2-(dihexylamino)ethyl, 3-(dihexylamino)propyl, 4-(dihexylamino)butyl, 5-(dihexylamino)pentyl, 6-(dihexylamino)hexyl, 8-(dihexylamino)octyl, 10-(dihexylamino)decyl, 12-(dihexylamino)dodecyl, 2-(methyl-ethyl-amino)ethyl, 2-(methyl-propyl-amino)ethyl, 2-(methyl-isopropyl-amino)ethyl, 2-(methyl-butyl-amino)ethyl, 2-(methyl-hexyl-amino)ethyl, 2-(methyl-octyl-amino)ethyl, 2-(ethyl-propyl-amino)ethyl, 2-(ethyl-isopropyl-amino)ethyl, 2-(ethyl-butyl-amino)ethyl, 2-(ethyl-hexyl-amino)ethyl, 2-(ethyl-octyl-amino)ethyl, 3-(methyl-ethyl-amino)propyl, 3-(methyl-propyl-amino)propyl, 3-(methyl-isopropyl-amino)propyl, 3-(methyl-butyl-amino)propyl, 3-(methyl-hexyl-amino)propyl, 3-(methyl-octyl-amino)propyl, 3-(ethyl-propyl-amino)propyl, 3-(ethyl-isopropyl-amino)propyl, 3-(ethyl-butyl-amino)propyl, 3-(ethyl-hexyl-amino)propyl, 3-(ethyl-octyl-amino)propyl, 4-(methyl-ethyl-amino)butyl, 4-(methyl-propyl-amino)butyl, 4-(methyl-isopropyl-amino)butyl, 4-(methyl-butyl-amino)butyl, 4-(methyl-hexyl-amino)butyl, 4-(methyl-octyl-amino)butyl, 4-(ethyl-propyl-amino)butyl, 4-(ethyl-isopropyl-amino)butyl, 4-(ethyl-butyl-amino)butyl, 4-(ethyl-hexyl-amino)butyl, 4-(ethyl-octyl-amino)butyl, 2-(N-piperidinyl)ethyl, 3-(N-piperidinyl)propyl, 4-(N-piperidinyl)butyl, 5-(N-piperidinyl)pentyl, 6-(N-piperidinyl)hexyl, 8-(N-piperidinyl)octyl, 10-(N-piperidinyl)decyl, 12-(N-piperidinyl)dodecyl, 2-(N-pyrrolidinyl)ethyl, 3-(N-pyrrolidinyl)propyl, 4-(N-pyrrolidinyl)butyl, 5-(N-pyrrolidinyl)pentyl, 6-(N-pyrrolidinyl)hexyl, 8-(N-pyrrolidinyl)octyl, 10-(N-pyrrolidinyl)decyl, 12-(N-pyrrolidinyl)dodecyl, 2-(N-morpholino)ethyl, 3-(N-morpholino)propyl, 4-(N-morpholino)butyl, 5-(N-morpholino)pentyl, 6-(N-morpholino)hexyl, 8-(N-morpholino)octyl, 10-(N-morpholino)decyl, 12-(N-morpholino)dodecyl, 2-(N'-methyl-N-piperazinyl)ethyl, 3-(N'-methyl-N-piperazinyl)propyl, 4-(N'-methyl-N-piperazinyl)butyl, 5-(N'-methyl-N-piperazinyl)pentyl, 6-(N'-methyl-N-piperazinyl)hexyl, 8-(N'-methyl-N-piperazinyl)octyl, 10-(N'-methyl-N-piperazinyl)decyl, 12-(N'-methyl-N-piperazinyl)dodecyl, 2-(N'-ethyl-N-piperazinyl)ethyl, 3-(N'-ethyl-N-piperazinyl)propyl, 4-(N'-ethyl-N-piperazinyl)butyl, 5-(N'-ethyl-N-piperazinyl)pentyl, 6-(N'-ethyl-N-piperazinyl)hexyl, 8-(N'-ethyl-N-piperazinyl)octyl, 10-(N'-ethyl-N-piperazinyl)decyl, 12-(N'-ethyl-N-piperazinyl)dodecyl, 2-(N'-isopropyl-N-piperazinyl)ethyl, 3-(N'-isopropyl-N-piperazinyl)propyl, 4-(N'-isopropyl-N-piperazinyl)butyl, 5-(N'-isopropyl-N-piperazinyl)pentyl, 6-(N'-isopropyl-N-piperazinyl)hexyl, 8-(N'-isopropyl-N-piperazinyl)octyl, 10-(N'-isopropyl-N-piperazinyl)decyl, 12-(N'-isopropyl-N-piperazinyl)dodecyl, 3-oxbutyl, 3-oxapentyl, 2,2-dimethyl-4-oxapentyl, 3,6-dioxaheptyl, 3,6-dioxaoctyl, 3,6,9-trioxadecyl, 3,6,9- trioxaundecyl, 4-oxapentyl, 4-oxahexyl, 4-oxaheptyl, 4,8-dioxanonyl, 4,8-dioxadecyl, 4,8-dioxaundecyl, 5-oxahexyl or 5,10-dioxaundecyl.

Furthermore, $R^2OH$ may be ethoxylated and/or propoxylated alcohols and mixed ethoxylated/propoxylated alcohols, such as $R^5$—(O—$CH_2$—$CH_2$)$_x$—OH or
$R^5$—(O—CH($CH_3$)—$CH_2$)$_x$—OH or $R^5$—(O—$CH_2$—CH($CH_3$))$_x$—OH, where
$R^5$ is $C_1$- to $C_{20}$-alkyl and
x is an integer from 1 to 20, or ethoxylated and/or propoxylated amino alcohols
$R^3{}_2N$(—$CH_2CH_2$—O)$_y$—H or
$R^3{}_2N$(—CH($CH_3$)—$CH_2$—O)$_y$—H or $R^3{}_2N$(—$CH_2$—CH($CH_3$)—O—)$_y$—H, where y is an integer from 1 to 4.

Dialkylaminoethanols are preferably used, dimethylaminoethanol, diethylaminoethanol and di-n-butylaminoethanol being particularly preferred.

In a particularly preferred embodiment, dialkylaminoethanols containing not more than 100, preferably not more than 50, particularly preferably not more than 20, in particular not more than 10, ppm of ethylene glycol are used.

In a further particularly preferred embodiment, dialkylaminoethanols containing not more than 100, preferably not more than 50, particularly preferably not more than 20, in particular not more than 10, ppm of vinyloxyethanol are used.

All transesterification catalysts described in the prior art are suitable for the novel process, preferably titanium, magnesium or aluminum alcoholates, particularly preferably titanium alcoholates, in particular titanium alcoholates of the alcohols which are present in the transesterification, i.e. $R^1OH$ and $R^2OH$.

1. Catalyst Preparation

Where titanium alcoholates are used, a lower titanium alcoholate $Ti(OR^4)_4$, preferably the isopropylate, isobutylate or n-butylate, is reacted with the higher alcohol $R^2OH$ (cf. equation III) at elevated temperatures (50-130° C.). The higher alcohol is used in molar excess (as a rule from 1:5 to 1:20).

Equation III $Ti(OR^4)_4 + R^2OH \rightleftharpoons Ti(OR^2)_4 + R^4OH$

For $R^2$, cf. equation (I)
$R^4$ is $C_1$-$C_8$-alkyl, preferably isopropyl, isobutyl or n-butyl
$R^2OH$ and $R^4OH$ should preferably fulfill the following conditions relating to their boiling points b.p.:

b.p.($R^2OH$)≧b.p.($R^4OH$)+20° C.

Under these conditions, it is technically simple to keep the losses of $R^2OH$ low and to separate off $R^4OH$ as completely as possible.

The alcohol $R^4OH$ formed in the reaction is separated off by distillation or rectification, if required under reduced pressure. This can, if required, be supported by stripping with a suitable unreactive gas. The resulting residue is the catalyst solution for the transesterification (Ti content: 2-10% by weight) and contains less than 400 ppm of $R^4OH$. Thus, virtually no foreign alcohol ($R^4OH$) is introduced into the transesterification mixture (<100 ppm in the mixture).

Of course, mixed titanium alcoholates can of course also be present in the catalyst solution, depending on the reaction according to equation III.

The distillate, predominantly the alcohol $R^4OH$, can advantageously be used for diluting the resulting residue (cf. below, stage 9).

2. Transesterification

The lower (meth)acrylate I used has, as a rule, the following composition:
99.0-99.95% by weight (Meth)acrylate
0.001-0.1% by weight Acetic ester
0.02-0.1% by weight Propionic ester
0.001-0.05% by weight Water Furthermore, the lower alkanol $R^1OH$, its dialkyl ether, (meth)acrylic acid and other, for example isomeric, (meth)acrylates may be present.

The higher alcohol $R^2OH$ usually has a purity of at least 99.0% by weight and a water content of 0.01-0.2% by weight.

In the case of dialkylaminoethanols, traces of higher homologs may also be present.

The ethylene glycol content should be not more than 100, preferably not more than 50, particularly preferably not more than 20, in particular not more than 10, ppm. The vinyloxyethanol content should be not more than 100, preferably not more than 50, particularly preferably not more than 20, in particular not more than 10, ppm.

Mixtures of higher alcohols may also be used for the transesterification.

The lower (meth)acrylate I, preferably the methyl or ethyl ester, is reacted with the higher alcohol $R^2OH$ in a molar ester:alcohol ratio of from 1:1 to 4:1 in the presence of the catalyst solution prepared under 1, the Ti content of the reaction mixture being, as a rule, 0.01-1% by weight.

The transesterification is carried out in one or more reactors, preferably in one reactor or two reactors (R1, R2) connected in series, having attached rectification columns (K1, K2, cf. FIG. 1) and condensers.

Figure 1:
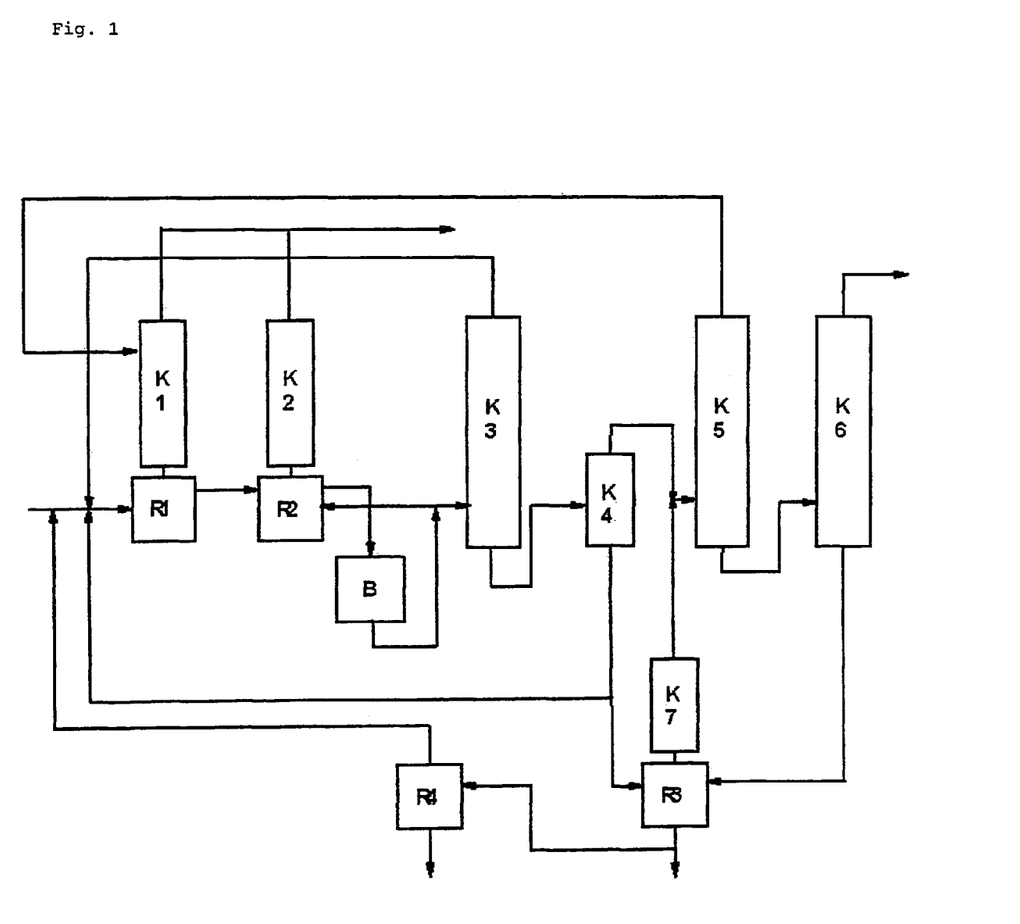

The uniform thorough mixing of the reaction solution is effected in a known manner, for example by stirring, pumped circulation or natural circulation, preferably by natural or forced circulation (not shown in FIG. 1).

The reaction temperature is as a rule 80-140° C., preferably 100-130° C., and the pressure is from 200 mbar to atmospheric pressure, preferably 300-800 mbar, particularly preferably 400-600 mbar.

The total residence time is in general 1-4, preferably 2-4, hours.

The heat can be supplied via wall heating and/or external or internal heat exchangers, for example tubular or plate heat exchangers.

The reaction zone can preferably be flushed continuously with a gas or gas mixture which is inert under the reaction conditions, for example nitrogen, air, air/nitrogen or nitrogen/oxygen mixtures, argon, helium, carbon dioxide or carbon monoxide. Particularly preferably, the purge gas is passed along the heat exchanger surfaces present, in particular where a pumped or natural circulation is present, as described in the German patent application with the title Process for the preparation of (meth)acrylates and with the same date of filing as the present document and Application number 101 27 938.8.

The transesterification mixture (reactor discharge) is conveyed into an insulated container (B) which serves as a buffer container for the subsequent distillation unit (K3).

A particularly preferred embodiment of stage 2 comprises continuously recycling the discharge of the buffer container (B) into one of the transesterification reactors (R1 or R2, preferably R2) and feeding only a part-stream (10-75%) to the downstream distillation K3.

In a further particularly preferred embodiment, the container B can be heated, for example, to 50 to 140° C. and is connected to the gas space of R2 and/or K2. The residence time in the container (B) is as a rule 0.5-1.5 hours. In this way, the remaining higher alcohol ($R^2OH$) is reacted in (B) and the resulting lower alkanol ($R^1OH$) is separated off via R2 and K2 and removed from the equilibrium. The advantage is a higher conversion in combination with less technical complexity and lower energy consumption.

3. Removal of the Lower Alkanol

The rectification columns are of a known design and have internals having separation activity (for example bubble trays, sieve trays or dual-flow trays) or contain dumped or stacked packings.

The column(s) attached to the reactor(s) has/have as a rule 10-30 theoretical plates. The reflux ratio is as a rule 5-15:1, preferably 7-12:1.

The condensers are likewise of a known design, for example tubular or plate heat exchangers.

The lower alkanol $R^1OH$ liberated during the transesterification in the reactors R1 and R2 is separated off together with a part of the lower (meth)acrylate I via the top of the rectification columns (K1, K2) attached to the reactors.

The distillation conditions, for example the number of theoretical plates and the reflux ratio, are chosen so that a nonazeotropic mixture is taken off at the top of the column, in which mixture the content of lower (meth)acrylate is higher compared with the azeotropic composition comprising lower alkanol and lower (meth)acrylate.

The distillation conditions are established so that the alkanol content of the condensate is, for example, 20-40% by weight in the case of methanol and 30-65, preferably 40-60, % by weight in the case of ethanol. As a rule, not more than 1, preferably not more than 0.5, particularly preferably not more than 0.3, % by weight of the higher alcohol $R^2OH$ is present.

This has the advantage that fewer theoretical plates and less reflux, and hence lower energy consumption, are required, resulting in lower thermal stress and less fouling, in particular of the evaporators, so that longer run-times of the plants can be achieved owing to fewer shutdowns.

A part of the condensate can be applied as reflux again at the top of the column, for example 40-99%, preferably 70-95% (not shown in FIG. 1).

The remaining part of the condensate can be recycled directly, i.e. without an additional purification step, into the synthesis of the lower alkyl (meth)acrylate I, where it can be reacted with (meth)acrylic acid again to give the starting ester, as described, for example, in the German patent application with the title Process for the preparation of (meth)acrylates with the same date of filing as the present document and Application number 101 27 941.8. There, it can advantageously be fed to the working-up process, particularly preferably an extraction process.

The column can be stabilized with the conventional stabilizers or mixtures thereof, such as N-oxyls, e.g. 4-hydroxy-2,2,6,6-tetramethylpiperidin-N-oxyl or 4-oxo-2,2,6, 6-tetramethylpiperidin-N-oxyl, phenols and naphthols, e.g. p-aminophenol, p-nitrosophenol, 2-tert-butylphenol, 4-tert-butylphenol, 2,4-di-tert-butylphenol, 2-methyl-4-tert-butylphenol, 4-methyl-2,6-tert-butylphenol (2,6-tert-butyl-p-cresol) or 4-tert-butyl-2,6-dimethylphenol, quinones, e.g. hydroquinone or hydroquinone monomethyl ether, aromatic amines, e.g. N,N-diphenylamine, phenylenediamines, e.g. N,N'-dialkyl-para-phenylenediamine, it being possible for the alkyl radicals to be identical or different and in each case, independently of one another, to be of 1 to 4 carbon atoms and straight-chain or branched, hydroxylamines, e.g. N,N-diethylhydroxylamine, phosphorus-containing compounds, e.g. triphenylphosphine, triphenyl phosphite or triethyl phosphite, or sulfur-containing compounds, e.g. diphenyl sulfide or phenothiazine.

Furthermore, these may also be degradation products or derivatives of stabilizers, for example the Michael adduct of (meth)acrylic acid or (meth)acrylate and hydroquinone.

The stabilization can be effected in the presence or absence of molecular oxygen.

The stabilization is preferably effected using phenothiazine, hydroquinone, hydroquinone monomethyl ether, 4-hydroxy-2,2,6,6-tetramethylpiperidin-N-oxyl, 4-oxo-2,2,6,6-tetramethylpiperidin-N-oxyl, 2,6-tert-butyl-p-cresol or mixtures thereof in amounts of, in each case, from 10 to 5 000 ppm. The addition can be effected in each case via the starting materials or via the recycle or reflux streams.

Stabilization is particularly preferably effected by means of the reflux to which 100-1 000 ppm of phenothiazine and 10-500 ppm of 4-hydroxy-2,2,6,6-tetramethylpiperidin-N-oxyl have been added. Preferably, the stabilization is effected by adding a solution of this stabilizer mixture in the lower (meth)acrylate.

Particularly preferably, the dissolved stabilizer mixture is sprayed onto condenser surfaces.

4. Removal of the Lower (meth)acrylate

The reaction mixture is subjected to a distillation or rectification (K3) in which substantially the remaining lower alkanol $R^1OH$ and the main amount, for example about 80-90%, of the lower (meth)acrylate I still present are separated off.

The rectification column is of a known design and has internals having separation activity (for example bubble trays, sieve trays or dual-flow trays) or contains dumped or stacked packings.

The column has, as a rule, 10-30 theoretical plates. The reflux ratio is, as a rule, from 1:3 to 1:15, preferably from 1:5 to 1:10.

The condensers and evaporators are likewise of a known design, for example tubular or plate heat exchangers.

The thorough mixing is effected in a known manner, for example by stirring, pumped circulation or natural circulation, preferably by natural or forced circulation (not shown in FIG. 1).

The bottom temperature is in general 100-170° C., preferably 120-160° C., particularly preferably 130-150° C. It has been found that these temperatures have an advantageous effect on the rate of formation of the Michael adducts, as described in EP-A 906 902, page 9, lines 21 to 28.

The pressure is in general from 20 mbar to atmospheric pressure, preferably 50-800 mbar, particularly preferably 100-500 mbar.

The statements made under 3 are applicable for the stabilization. The condensates stabilized with 100-1 000 ppm of phenothiazine and 10-500 ppm of 4-hydroxy-2,2,6, 6-tetramethylpiperidin-N-oxyl (see above) can be recycled partly, e.g. 5-20%, as reflux to the column. The remainder can preferably be fed to the transesterification reactor (R1), for example via the attached column K1 or directly into the reactor R1.

5. Catalyst Removal

The transesterification mixture substantially freed from the lower (meth)acrylate is subjected to a distillation or rectification, preferably a thin-film or flash evaporation, particularly preferably a flash evaporation (K4), with or without the use of a stripping gas, in general at 100-170° C., preferably 125-160° C., particularly preferably 130-150° C., under in general 10-500, preferably 20-300, particularly preferably 20-200, mbar.

In a particularly preferred embodiment, the flash evaporator is additionally equipped with a circulation evaporator.

There, substantially the desired ester IV and low boilers (e.g. starting materials) distill off and a bottom product which mainly comprises catalyst, stabilizers and Michael adducts is obtained.

This bottom mixture to be recycled partly, preferably in an amount of 60-95%, into the transesterification, and the remainder can be fed to an unlimited residue treatment (R3), in which desired ester still present is recovered and at the same time the Michael adducts, e.g. II and III, are cleaved back into the corresponding alcohols and (meth)acrylates and are separated off.

It may also be expedient to interchange steps 4 and 5, i.e. first to separate the discharge from the transesterification, in an apparatus as described under 5, from the bottom product which mainly comprises catalyst, stabilizer and Michael adducts, and then to separate off substantially the lower alkanol and the lower (meth)acrylate in a distillation or rectification as described under 4.

In this case, the bottom product from K4 is passed as before into the residue treatment R3 and the bottom product from K3, if necessary together with the distillate from K7, is passed into K5 (low boiler removal). This has the advantage that the reaction mixture is exposed to the catalyst for a shorter time so that catalyst-induced secondary or subsequent reactions are reduced.

Depending on the type of lower ester, it may be advantageous to give preference to step 5 and to combine steps 4 and 6, but, for the methyl and ethyl (meth)acrylates as lower esters, however, the steps are preferably carried out in the sequence 4, 5 and 6.

6. Low Boiler Removal

The distillate obtained under 5, separated from the catalyst and mainly comprising 85-95% of desired ester IV, 5-15% of higher alcohol $R^2OH$, 1-2% of lower (meth) acrylate 1 and 1-2% of Michael adducts, e.g. II or III, is separated, together with the distillate of the residue treatment (K7), in a further distillation step (K5), into a distillate comprising lower and higher (meth)acrylates and a higher alcohol and a bottom product mainly comprising the desired ester.

The rectification column is of a known design and has internals having separation activity (for example bubble trays, sieve trays or dual-flow trays) or contains dumped or stacked packings.

The column has, as a rule, 10-30 theoretical plates. The reflux ratio is, as a rule, from 10:1 to 1:10, preferably from 1:2 to 5:1.

The condensers and evaporators are likewise of a known design, for example tubular or plate heat exchangers.

On the one hand, the stabilized distillate (for example in an amount of 20-50%) can be fed to the reactor R1 and/or R2 and/or via the column (K1 and/or K2) attached to the reactor back to the transesterification, the feed preferably being located in the lower half of the column, and, on the other hand, said distillate can be fed as reflux back to the distillation column.

The statements made under 3 are applicable for the stabilization, the latter preferably being effected with 100-1 000 ppm of phenothiazine and 10-500 ppm of 4-hydroxy-2,2,6,6-tetramethylpiperidin-N-oxyl.

7. Distillation of Pure Ester

The desired ester IV is distilled off from the bottom product obtained under 6, in a further distillation step (K6), via the top of the column.

The rectification column is of a known design and has internals having separation activity (for example bubble trays, sieve trays or dual-flow trays) or contains dumped or stacked packings.

The column has, as a rule, 10-30 theoretical plates. The reflux ratio is, as a rule, from 10:1 to 1:10, preferably from 1:2 to 5:1.

The condensers and evaporators are likewise of a known design, for example tubular or plate heat exchangers.

The condensation can also be operated by means of a quench of conventional design which is operated using stabilized pure product (at a quench temperature of from 20 to. 40° C.).

The desired ester, i.e. the higher (meth)acrylate IV is stabilized with a storage stabilizer, e.g. hydroquinone, hydroquinone monomethyl ether, 4-hydroxy-2,2,6,6-tetramethylpiperidin-N-oxyl, 4-oxo-2,2,6,6-tetramethylpiperidin-N-oxyl, 2,6-tert-butyl-p-cresol or mixtures thereof, preferably 2,6-tert-butyl-p-cresol and/or hydroquinone monomethyl ether, particularly preferably hydroquinone monomethyl ether in amounts of in each case 5-500, preferably 10-300, particularly preferably 10-200, ppm.

10-50% of the distillate can be applied as reflux back to the top of the column (not shown in FIG. 1).

The bottom product, mainly comprising remaining desired ester, Michael adducts, stabilizer and polymers, can be fed at least partly, together with the bottom product from 5 to the residue treatment.

It is also possible to combine steps 6 and 7, it being possible for the distillate containing the desired ester and obtained from 5, if required in combination with the distillate from the residue treatment, to be separated in a further distillation unit into a low boiler fraction, which mainly comprises the lower and higher (meth)acrylate and higher alcohol and can be recycled to the transesterification, into a high boiler fraction (bottom product), which mainly comprises desired ester, Michael adducts and inhibitors and is advantageously fed to the residue treatment, and into a medium boiler fraction which substantially comprises the desired ester. The desired ester, preferably in gaseous form, is removed via a side take-off in the lower column region, preferably in the lower half, particularly preferably in the lower third, condensed, and stabilized as described above.

The bottom temperature is as a rule 110-130° C. and the corresponding pressure is 100-200 mbar.

8. Residue Treatment

The combined bottom products of stages 5 and 7 are heated in a reactor (R3), if required with attached column (K7), to 100-220° C., preferably 120-200° C., particularly preferably 130-180° C., in the presence or absence of an acidic or basic catalyst, e.g. sulfuric acid, phosphoric acid, sulfonic acids, such as para-toluenesulfonic acid or dodecylsulfonic acid, acidic metal oxides or ion exchangers or metal alcoholates, alkali metal carbonates or alkali metal hydroxides, preferably without additional catalyst. This temperature is sufficient to result in cleavage of the Michael adducts back into the parent components alcohol and ester (reverse reaction to equation II). The cleavage rate under said reaction conditions is in general about 50% by weight or more.

In a preferred embodiment, the cleavage product can be separated off via K7, if required with the use of a stripping gas, and can be fed back to the low boiler distillation (K5) or the transesterification R1 or R2 and/or K1 or K2.

Consequently, no special, technically complicated measures are required in order to minimize the formation of Michaela adducts during the synthesis and/or during the working-up.

9. Working-Up of the Residue

The discharge of the residue treatment, which mainly comprises polymers, stabilizers and the catalyst (e.g. the titanate of the higher alcohol), is reacted at 50-180° C., preferably 70-170° C., particularly preferably 80-150° C., with a high-boiling, hydroxyl-containing substance in R4. This is preferably an economical mono- or polyalcohol, if desired a mixture thereof or a residue which contains it.

Those hydroxyl-containing substances whose boiling point at atmospheric pressure is at least 200° C. are high-boiling.

The alcohols ($R^2OH$ and $R^1OH$) liberated by transesterification are preferably distilled off continuously, if necessary under reduced pressure, for example via a column, and can be recycled directly to the transesterification (R1).

Examples of suitable high-boiling alcohols are glycerol, residues of the preparation of 2-ethylhexanol, residues or secondary fractions of the polyethylene glycol or trimethylolpropane preparation. One of the advantages is that useful alcohols are recovered (increase in yield) and the residues, which are advantageously incinerated, can be better handled. By a specific choice of the time and amount of the high-boiling alcohol, it is in fact possible to vary the viscosity of the residue within wide limits.

The distillate of the catalyst preparation from stage 1 can also advantageously be used for establishing the viscosity, for example by dilution.

10. Utilization of the Azeotropic Mixture

The discharged mixture comprising lower alkanol and the corresponding (meth)acrylate from stage 2 or 3 can be reacted in a known manner directly, i.e. without prior purification, in the presence of strong acids, e.g. sulfuric acid or sulfonic acid, with (meth)acrylic acid (Kirk Othmer, Encyclopedia of Chemical Technology, 4th ed., 1994, pages 301-302). The lower alkanol is converted into the corresponding (meth)acrylate, which can be used again as starting material for the novel transesterification.

In a further preferred embodiment, the mixture is fed not to the transesterification reactor but at least partly to the working-up in a plant for the preparation of the lower (meth)acrylate. Preferably, the mixture is fed to the wash column in which the separation of the alkanol from the desired ester is carried out, the alkanol being recovered from the aqueous phase and reused in the esterification (ibid. page 301).

Owing to the use of the special stabilizer system in the individual stages for working up the transesterification mixture, the formation of polymer and deposits is substantially prevented.

There is therefore no need to maintain any additional special conditions in the various distillation steps.

The time-on-stream of the plant under the conditions described is in general at least 150 days.

The content of ethylene glycol di(meth)acrylate and vinyloxyethyl (meth)acrylate in the dialkylaminoethyl (meth) acrylates prepared according to the invention is in general not more than 100, preferably not more than 50, particularly preferably not more than 20, in particular not more than 10, ppm.

The dialkylaminoalkyl (meth)acrylate prepared according to the invention, in particular dialkylaminoethyl (meth) acrylate and especially dimethylaminoethyl (meth)acrylates, are useful monomers for the preparation of copolymers. They are used as monomers in the present form or after quaternization in the polymerization.

Conventional quaternizing agents are, for example, benzyl halides, such as benzyl chloride, alkyl halides, such as methyl chloride, ethyl chloride, methyl bromide, ethylene dichloride or allyl chloride, alkylene oxides, such as ethylene oxide, propylene oxide, styrene oxide, isobutylene oxide or vinyloxirane, preferably ethylene oxide or propylene oxide and particularly preferably ethylene oxide, alkyl phosphites or alkyl phosphonates, such as trimethyl phosphite or triethyl phosphite, dialkyl sulfates, such as dimethyl sulfate or diethyl sulfate, dialkyl carbonates, such as dimethyl carbonate, diethyl carbonate or di-n-butyl carbonate, chlorohydrin or epichlorohydrin.

In particular those copolymers which contain quaternized monomers as polymerized units are used in water treatment, for example as ion exchange resins or as a component of membranes.

The example which follows illustrates the novel process without restricting it.

ppm and percentage data used in this document are percentages by weight and ppm by weight, unless stated otherwise.

EXAMPLE 1

Preparation of the Catalyst

In a stirred reactor having wall heating and an attached packed column, a mixture of 1 300 parts of dimethylaminoethanol and 400 parts of tetraisopropyl titanate was heated to 100° C. and the isopropanol formed was discharged continuously via the column (top temperature 70° C., 300 mbar). 250 parts of distillate were obtained in the course of 4 hours and the residue contained 4.6% by weight of titanium and not more than 0.1% by weight of isopropanol and was used directly as a transesterification catalyst.

EXAMPLE 2

Preparation of Dimethylaminoethyl Acrylate

In continuous operation, 266 parts of dimethylaminoethanol containing less than 10 ppm each of ethylene glycol and vinyloxyethanol, 780 parts of a mixture of methyl acrylate and the distillate from the methyl acrylate separation, 17 parts of catalyst solution from example 1 and 69 parts of recycle catalyst (bottom product of the catalyst removal) were fed per hour to the first reactor of the reactor cascade consisting of two reactors. The reactors were equipped in each case with an attached packed column and two condensers arranged in series. Heat was supplied via external heat exchangers. In addition, 270 parts per hour of the condensate of the low boiler removal were added via a feed in the middle of the column of the first reactor. The reaction temperature was 100° C. The methanol formed in the transesterification was discharged as a mixture with methyl acrylate at the top of the reactor columns (63° C.) and condensed. The combined condensates were partly recycled as reflux into the columns (in each case about 2 100 parts) and the remainder (280 parts) was discharged and was collected for use in the methyl acrylate preparation. The dimethylaminoethanol content was less than 0.05%.

The condensates were stabilized by adding 56 parts of a solution of 0.5% of phenothiazine and 0.05% of 4-hydroxy-2,2,6,6-tetramethylpiperidin-N-oxyl in methyl acrylate to the first condenser of the column of the first reactor and 115 parts of this solution to the first condenser of the column of the second reactor. The combined condensates contained about 36% by weight of methanol and about 64% by weight of methyl acrylate.

The discharge of the second reactor (1 300 parts) was fed to an insulated container whose average temperature was 88° C. The discharge of this container was fed partly back to the reactor R2 and partly (1:1) to a packed column (feed above the middle of the column, 1 300 parts), where it was separated into a top product (top temperature 56° C., 300 mbar) and a catalyst-containing bottom product (bottom temperature 130° C.) which substantially comprised dimethylaminoethyl acrylate and dimethylaminoethanol.

The product was stabilized by spraying 95 parts of stabilizer solution described above into the top of the condenser. The condensate was mixed with 170 parts of methyl acrylate and fed partly (98 parts/h) as reflux back to the column, and the remainder (780 parts/h) was fed to the first reactor. It substantially comprised 96.5% of methyl acrylate, 1.5% of dimethylaminoethyl acrylate and 1.3% of methanol.

The bottom product was subjected to a flash evaporation (130° C., 65 mbar), resulting in a distillate which was stabilized with 0.1% of hydroquinone monomethyl ether and contained about 90% of dimethylaminoethyl acrylate. The catalyst-containing bottom product obtained was partly recycled into the first reactor (69 parts/h) and the remainder (30 parts/h) was fed to the residue treatment.

The distillate (685 parts), together with the distillate of the residue treatment (137 parts), was separated in a further packed column (feed below the middle of the column) into a low boiler fraction (top temperature 73° C., 60 mbar) and a bottom product which substantially comprised dimethylaminoethyl acrylate (97.8%) and Michael adduct (1.9%). The low boiler fraction was stabilized by spraying 19 parts/h of the stabilizer solution described into the top of the condenser and substantially comprised 50.6% of dimethylaminoethyl acrylate, 29.6% of dimethylaminoethanol and 21.9% of methyl acrylate. 270 parts of the low boiler fraction were fed to the 1st reactor via the column, and the remainder was applied as reflux to the top of the low boiler column. In a further distillation step (packed column, feed above the 1st third of the column), dimethylaminoethyl acrylate was isolated as top product (85° C., 60 mbar) from the bottom product. The distillate was stabilized with 0.1 part of hydroquinone monomethyl ether as a 1% strength by weight solution in pure product, 380 parts thereof were recycled as reflux into the top of the column and 445 parts were removed as pure product. The purity was 99.9%, the yield was 98%, based on dimethylaminoethanol, and the contents of ethylene glycol diacrylate and vinyloxyethyl acrylate were each less than 10 ppm.

The residue of the distillative purification and the residue discharged from the catalyst removal were fed to a reactor having an attached packed column and the remaining dimethylaminoethyl acrylate was distilled off at 140° C. and at the same time the Michael adducts were cleaved. 137 parts/h of distillate were isolated and added to the feed to the low boiler distillation. The residue contained no solid and was pumpable.

EXAMPLE 3

Working-Up of the Residue

In a reactor, the residue of the residue treatment was mixed 1:1 with glycerol and heated to 160° C. The dimethylaminoethanol liberated was discharged continuously in gaseous form and condensed. 37 parts of a distillate which substantially comprised dimethylaminethanol were obtained from 100 parts of residue.

EXAMPLE 4

In continuous operation, 680 parts of dimethylaminoethanol, 2 016 parts of a mixture of ethyl acrylate and the distillate of the ethyl acrylate removal, 70 parts of catalyst solution from example 1 and 110 parts of recycle catalyst (bottom product of the catalyst removal) were fed per hour to the first reactor of a reactor cascade consisting of two reactors. The reactors were each equipped with an attached packed column and a condenser. Heat was supplied via external heat exchangers. In addition, 236 parts per hour of the condensate of the low boiler removal were added via a feed in the middle of the column of the first reactor. The discharge of the second reactor was fed to a container equipped with a circulation evaporator and connected on the gas side to the column of the second reactor. The reaction temperatures were 110 and 115° C., respectively, and 119° C. in the container. The ethanol formed during the transesterification was discharged as a mixture with ethyl acrylate (48% of ethanol) at the top of the reactor columns and condensed. The combined condensates were partly recycled as reflux into the columns (in each case about 2 100 parts) and the remainder (806 parts) was discharged and collected for use in the ethyl acrylate preparation. The condensates were stabilized by adding 120 parts of a solution of 0.5% of phenothiazine and 0.05% of 4-hydroxy-2,2,6,6-tetramethylpiperidin-N-oxyl in ethyl acrylate to each condenser. The combined condensates contained about 48% by weight of ethanol and about 52% by weight of ethyl acrylate, and the dimethylaminoethanol content was less than 0.1%.

The discharge of the container was fed to a packed column (feed in the middle of the column), where it was separated into the top product (top temperature 88° C., 500 mbar) and a catalyst-containing bottom product (bottom temperature 140° C.).

The top product was stabilized by spraying 110 parts of the stabilizer solution described above into the top of the condenser. The condensate was mixed with 1 170 parts of ethyl acrylate and partly (380 parts/h) recycled as reflux to the column, and the remainder (2 016 parts/h) was fed to the first reactor.

The bottom product was fed to a flash evaporator which was additionally equipped with a circulation evaporator (135° C., 80 mbar). The distillate was stabilized with 50 parts of stabilizer solution (see above) and contained about 90% of dimethylaminoethyl acrylate. The bottom product was partly (110 parts) fed to the first reactor and the remainder (70 parts/h) was fed to the residue treatment.

The ratio of the Michael adduct formation (EP-A 906 902, page 9) was negative (−1.3%), calculated over both distillation stages, which indicates partial reduction (cleavage) of the adducts under the stated conditions.

The further working-up of the distillate of the flash evaporation, which working-up was carried out analogously to example 2, gave 1 189 parts of dimethylaminoethyl acrylate in a purity of 99.9%, which corresponds to a yield of 97.9%, based on dimethylaminoethanol.

EXAMPLE 5

The procedure was analogous to example 4 but the bottom temperature in the ethyl acrylate removal was 110° C. and the temperature in the catalyst removal (flash evaporator) was 110° C.

The ratio of the Michael adduct formation, determined on the basis of the gas chromatographic analyses of the individual streams, was about +0.1%, i.e. there was a slight increase in the Michael adduct.

We claim:

1. A process for preparation of (meth)acrylate IV by transesterification of a (meth) acrylate I with an alcohol $R^2OH$ which has at least one carbon atom more than the alcohol component ($R^1O$—) in the (meth)acrylate I to be transesterified, as follows:

wherein R is H or $CH_3$, and $R^1$ is a straight-chain or branched, saturated or unsaturated, aromatic, aliphatic or cycloaliphatic group, and may contain hetero atoms or aromatic substituents; and $R^2$ is a straight-chain or branched, saturated or unsaturated, aliphatic group, which may contain hetero atoms and may contain aromatic substituents; or $R^2$ is a saturated or unsaturated cycloaliphatic group or aromatic group and may contain aromatic substituents;

in the presence of a catalyst or catalyst mixture, wherein the lower alkanol $R^1OH$ liberated in the transesterification is separated off together with a part of the lower (meth)acrylate I and is fed, without an additional purification step, into a plant for the production and/or working-up of the (meth) acrylate I and, from the discharge of the transesterification reaction, either first the major amount of the (meth)acrylate I is separated off and is then separated by distillation from the catalyst used (catalyst removal), or is first separated by distillation from the catalyst used (catalyst removal) and then the major amount of the (meth)acrylate I is separated off and then components having a lower boiling point than the (meth)acrylate IV are substantially separated from the resulting mixture by distillation (low boiler removal) and then the (meth)acrylate IV is purified by distillation (distillative purification).

2. A process as claimed in claim 1, wherein alcohol $R^2OH$ is a member selected from the group consisting of n-propanol, isopropanol, allyl alcohol, n-butanol, 1-methylpropanol, 2-methylpropanol, tert-butanol, n-pentanol, 1-methylbutanol, 2-methylbutanol, 3-methylbutanol, 2,2-dimethylpropanol, n-hexanol, 1-methylpentanol, 2-methylpentanol, 3-methylpentanol, 4-methylpentanol, 1,1-dimethylbutanol, 2,2-dimethylbutanol, 3,3-dimethylbutanol, 1,2-dimethylbutanol, n-heptanol, 1-methylhexanol, 2-methylhexanol, 3-methylhexanol, 4-methylhexanol, 1,2-dimethylpentanol, 1,3-dimethylpentanol, 1,1-dimethylpentanol, 1,1,2,2-tetramethylpropanol, benzyl alcohol, n-octanol, 2-ethylhexanol, n-nonanol, 1-methyloctanol, 2-methyloctanol, n-decanol, n-undecanol, 1-methyldecanol, 2-methyldecanol, n-dodecanol, 2,4-diethyloctanol, cyclopentanol, cyclohexanol, 4-tert-butylcyclohexanol, cycloheptanol, cyclododecanol, 2-(dimethylamino)ethanol, 3-(dimethylamino)propanol, 4-(dimethylamino)butanol, 5-(dimethylamino)pentanol, 6-(dimethylamino)hexanol, 8-(dimethylamino)octanol, 10-(dimethylamino)decanol, 12-(dimethylamino)dodecanol, 2-(diethylamino)ethanol, 3-(diethylamino)propanol, 4-(diethylamino)butanol, 5-(diethylamino)peutanol, 6-(diethylamino)hexanol, 8-(diethylamino)octanol, 10-(diethylamino)decanol, 12-(diethylamino)dodecanol, 2-(di(isopropyl)amino)ethanol, 3-(di(isopropyl)-amino)propanol, 4-(di(ispropyl)amino)butanol, 5-(di(isopropyl)amino)pentanol, 6-(di(isopropyl)amino)-hexanol, 8-(di(isopropyl)amino)octanol, 10-(di(isopropyl)-amino)decanol, 12-(di(isopropyl)amino)dodecanol, 2-(dibutylamino)ethanol, 3-(dibutylamino)propanol, 4-(dibutylamino)butanol, 5-(dibutylamino)pentanol, 6-(dibutylamino)hexanol, 8-(dibutylamino)octanol 10-(dibutylamino)decanol, 12-(dibutylamino)dodecanol, 2-(dihexylamino)ethanol, 3-(dihexylamino)propanol, 4-(dihexylamino)butanol, 5-(dihexylamino)pentanol, 6-(dihexylamino)hexanol, 8-(dihexylamino)octanol, 10-(dihexylamino)decanol, 12-(dihexylamino)dodecanol, 2-(methylethylamino)ethanol, 2-(methylpropylamino)ethanol, 2-(methylisopropylamino)ethanol, 2-(methylbutylamino) ethanol, 2-(methylhexylamino)ethanal, 2-(methyloctylamino)ethanol, 2-(ethylpropylamino)ethanol, 2-(ethylisopropylamino)ethanol, 2-(ethylbutylamino)ethanol, 2-(ethythexylamino)ethanol, 2-(ethyloctylamino)ethanol, 3-(methyletylamino)propanol, 3-(methylpropylamino)propanol, 3-(methylisopropylamino)-propanol, 3-(methylbutylamino)propanol, 3-(methylhexylamino)propanol, 3-(methyloctylamino)propanol, 3-(ethylpropylamino)propanol, 3-(ethylisopropylamino)-propanol, 3-(ethylbutylamino)propanol, 3-(ethylhexylamino)propanol, 3-(ethyloctylamino) propanol, 4-(methylethylamino)butanol, 4-(methylpropylamino)butanol, 4-(methylisopropylamino)butanol, 4-(methylbutylamino)butanol, 4-methylhexylamino)butanol, 4-(methyloctylamino)butanol, 4-(ethylpropylamino) butanol, 4-(ethylisopropylamino)butanol, 4-(ethylbutylamino)butanol, 4-(ethylhexylamino)butanol, 4-(ethyloctylamino)butanol, 3-oxabutanol, 3-oxapentanol, 2,2-dimethyl-4-oxapentanol, 3,6-dioxaheptanol, 3,6-dioxaoctanol, 3,6,9-trioxadecanol, 3,6,9-trioxaundecanol, 4-oxapentanol, 4-oxahexanol, 4-oxaheptanol, 4,8-dioxanonanol, 4,8-dioxadecanol, 4,8-dioxaundecanol, 5-oxahexanol, 5,10-dioxaundecanol, ethoxylated and/or propoxylated alcohols and mixed ethoxylated/propoxylated alcohols, wherein the lower alkanol $R^1OH$ is a member selected from the group consisting of methanol, ethanol, n-propanol, isopropanol, n-butanol, isobutanol, 2-butanol and tert-butanol.

3. A process as claimed in claim 2, wherein the alcohol $R^2OH$ is selected from dimethylaminoethanol, diethylaminoethanol, di-n-butylaminoethanol, 3dimethylaminopropanol, 3diethylaminopropanol and 3di-n-butylaminopropanol.

4. A process as claimed in claim 1, wherein the catalyst removal is carried out at from 125 to 160° C.

5. A process as claimed in claim 1, wherein the removal of the (meth)acrylate I is carried out at from 120 to 160° C.

6. A process as claimed in claim 1, wherein the boiling point of the alcohol $R^2OH$ is 20° C. or more above that of the alcohol $R^1OH$.

7. A process as claimed claim 1, wherein the distillate removed from the column attached to the reactor or from the columns attached to the reactors contains 20-40% by weight of methanol in the case of methanolate as the alcohol component ($R^1O—$) in the (meth)acrylate to be transesterified and 30-65% by weight of ethanol in the case of ethanolate as the alcohol component ($R^1O—$) in the (meth)acrylate I to be transesterified.

8. A process as claimed in claim 1, wherein the residue of the catalyst removal is recycled at least partly to the transesterification.

9. A process as claimed in claim 1, wherein the residue of the catalyst removal is subjected, separately or together with the residue of the distillative purification, at least partly to a thermal and/or catalytic treatment.

10. A process as claimed in claim 8, wherein a distillate removed from the thermal and/or catalytic treatment is recycled to the low boiler removal and/or the transesterification.

11. A process as claimed in claim 8, wherein the bottom discharge of the thermal and/or catalytic treatment is reacted with a high-boiling hydroxyl-containing substance and the low boilers distilled off thereby are recycled to the transesterification.

12. A process as claimed in claim 1, wherein at least a part of the discharge of the transesterification is recycled from an insulated buffer container to the transesterification.

13. A process as claimed in claim 12, wherein the insulated buffer container is heated.

14. A process as claimed in claim 12, wherein the insulated buffer container is connected to the last reactor of the transesterification and/or to the column attached to said reactor.

15. A process as claimed in claim 1, wherein the catalyst used is a titanium alcoholate $Ti(OR^2)_4$.

16. A process as claimed in claim 15, wherein the titanium alcoholate $Ti(OR^2)_4$ is obtained from a lower titanium alcoholate $Ti(OR^4)_4$, where $R^4$ is $C_1$-$C_8$-alkyl, by transesterification with a higher alcohol $R^2OH$, where $R^2$ has the above meaning and $R^2OH$ and $R^4OH$ fulfill the condition b.p. ($R^2OH$)$\geq$b.p. ($R^4OH$)+20° C. with regard to their boiling points b.p.

17. A process as claimed in claim 16, wherein the alkanol $R^4OH$ formed in the transesterification is removed from the transesterification.

18. A process as claimed in claim 16, wherein the reaction mixture obtained contains less than 400 ppm of $R^4OH$.

19. A process as claimed in claims 1, which is carried out at least partly in the presence of at least one of the following stabilizers: phenothiazine, 4-methyl-2,6-tert-butylphenol, hydroquinone monomethyl ether, 4-hydroxy-2,2,6,6-tetramethylpiperidin-N-oxyl and 4-oxo-2,2,6,6-tetramethylpiperidin-N-oxyl.

20. A process as claimed claim 1, wherein $R^2$ is 2-(dimethylamino)ethyl, 2-(di-n-butylamino)ethyl or 2-(diethylamino)ethyl and $R^1$ is methyl or ethyl.

21. A process as claimed in claim 2, wherein the catalyst removal is carried out at from 125 to 160° C.

22. A process as claimed in claim 2, wherein the removal of the (meth)acrylate I is carried out at from 120 to 160° C.

23. A process as claimed in claim 2, wherein the boiling point of the alcohol $R^2OH$ is 20° C. or more above that of the alcohol $R^1OH$.

24. A process as claimed claim 2, wherein the distillate removed from the column attached to the reactor or from the columns attached to the reactors
    contains 20-40% by weight of methanol in the case of methanolate as the alcohol component ($R^1O—$) in the (meth)acrylate to be transesterified and
    30-65% by weight of ethanol in the case of ethanolate as the alcohol component ($R^1O—$) in the (meth)acrylate I to be transesterified.

25. A process as claimed in claim 2, wherein the residue of the catalyst removal is recycled at least partly to the transesterification.

26. A process as claimed in claim 2, wherein the residue of the catalyst removal is subjected, separately or together with the residue of the distillative purification, at least partly to a thermal and/or catalytic treatment.

27. A process as claimed in claim 25, wherein a distillate removed from the thermal and/or catalytic treatment is recycled to the low boiler removal and/or the transesterification.

28. A process as claimed in claim 25, wherein the bottom discharge of the thermal and/or catalytic treatment is reacted with a high-boiling hydroxyl-containing substance and the low boilers distilled off thereby are recycled to the transesterification.

29. A process as claimed in claim 2, wherein at least a part of the discharge of the transesterification is recycled from an insulated buffer container to the transesterification.

30. A process as claimed in claim 29, wherein the insulated buffer container is heated.

31. A process as claimed in claim 29, wherein the insulated buffer container is connected to the last reactor of the transesterification and/or to the column attached to said reactor.

32. A process as claimed in claim 2, wherein the catalyst used is a titanium alcoholate $Ti(OR^2)_4$.

33. A process as claimed in claim 32, wherein the titanium alcoholate $Ti(OR^2)_4$ is obtained from a lower titanium alcoholate $Ti(OR^4)_4$, where $R^4$ is $C_1$-$C_8$-alkyl, by transesterification with a higher alcohol $R^2OH$, where $R^2$ has the above meaning and $R^2OH$ and $R^4OH$ fulfill the condition b.p. ($R^2OH$)$\geq$b.p. ($R^4OH$)+20° C. with regard to their boiling points b.p.

34. A process as claimed in claim 33, wherein the alkanol $R^4OH$ formed in the transesterification is removed from the transesterification.

35. A process as claimed in claim 33, wherein the reaction mixture obtained contains less than 400 ppm of $R^4OH$.

36. A process as claimed in claims 2, which is carried out at least partly in the presence of at least one of the following stabilizers: phenothiazine, 4-methyl-2,6-tert-butylphenol, hydroquinone monomethyl ether, 4-hydroxy-2,2,6,6-tetramethylpiperidin-N-oxyl and 4-oxo-2,2,6,6-tetramethylpiperidin-N-oxyl.

37. A process as claimed claim 2, wherein $R^2$ is 2-(dimethylamino)ethyl, 2-(di-n-butylamino)ethyl or 2-(diethylamino)ethyl and $R^1$ is methyl or ethyl.

* * * * *